United States Patent [19]

Sunderland

[11] 4,391,042
[45] Jul. 5, 1983

[54] CUTTING APPARATUS FOR CUTTING A NON-CIRCULAR OPENING

[76] Inventor: Ned E. Sunderland, 209 Melbourne Way, Lexington, Ky. 40503

[21] Appl. No.: 274,748

[22] Filed: Jun. 18, 1981

[51] Int. Cl.³ .............................................. B26B 27/00
[52] U.S. Cl. ........................................ 30/316; 30/123; 33/191
[58] Field of Search ................. 30/123, 316, 358, 359, 30/368, 130, 301, 315, 340, 342; 33/191

[56] References Cited

U.S. PATENT DOCUMENTS

| | | | |
|---|---|---|---|
| 1,513,478 | 10/1924 | Bourgue | 30/130 |
| 2,086,435 | 7/1937 | Rapp | 30/316 X |
| 2,586,823 | 2/1952 | Huhn | 30/316 X |
| 3,114,973 | 12/1963 | Kennedy | 30/342 |
| 4,010,543 | 3/1977 | Nusbaum | 30/316 |
| 4,277,891 | 7/1981 | Dick | 30/316 |

FOREIGN PATENT DOCUMENTS 2003906 8/1971 Fed. Rep. of Germany ........ 33/191

636815 5/1950 United Kingdom .................. 30/368

Primary Examiner—Jimmy C. Peters
Attorney, Agent, or Firm—Frank C. Leach, Jr.

[57] ABSTRACT

A body has a recess in one surface and within which is disposed a non-circular cutting element retained therein by an epoxy. The non-circular cutting element has its cutting edge formed by beveling its inner surface. The non-circular cutting element extends sufficiently beyond the one surface of the body to be able to penetrate into a face plate, which is utilized with a stoma and in which the non-circular opening is to be cut for use with the stoma of the same shape. A circular template of a clear plastic is removably mounted on the one surface of the body and has a plurality of circles of varying diameters thereon to center the non-circular cutting element relative to a face plate adhesive blank of one of the varying diameters to enable cutting of the same non-circular opening in the adhesive blank. The template has a pair of parallel lines along its circumference to align with a tab on the adhesive blank.

19 Claims, 32 Drawing Figures

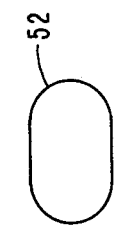
FIG. 8B 51
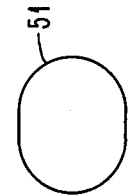
FIG. 8C 52
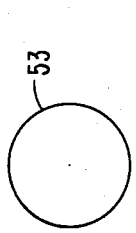
FIG. 8 53
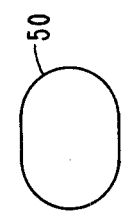
FIG. 8A 50
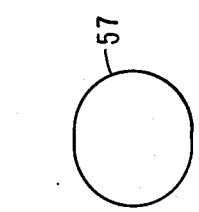
FIG. 9D 57
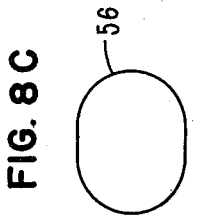
FIG. 9C 56
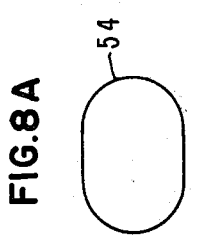
FIG. 9B 55
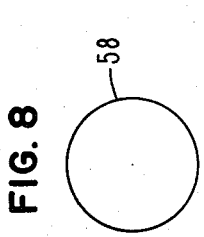
FIG. 9 58
FIG. 9A 54
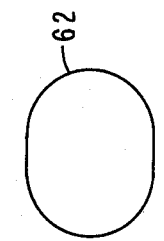
FIG. 10D 62
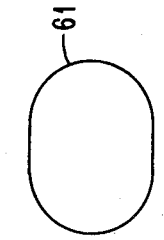
FIG. 10C 61
FIG. 10F 64
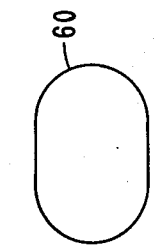
FIG. 10B 60
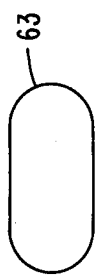
FIG. 10E 63
FIG. 10A 59
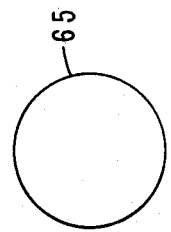
FIG. 10 65

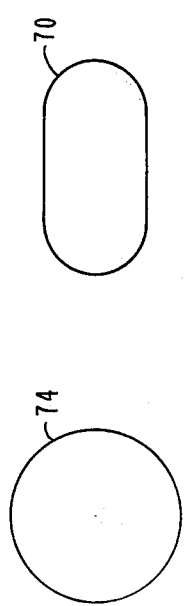
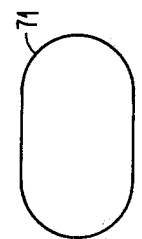
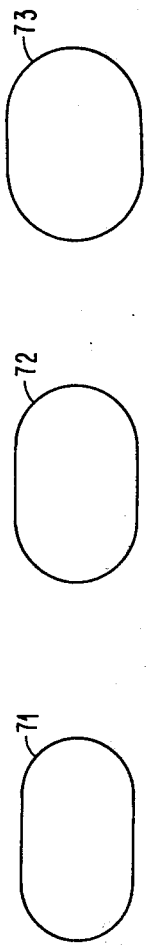
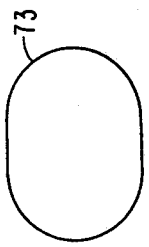
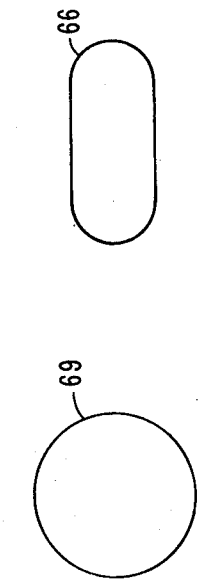
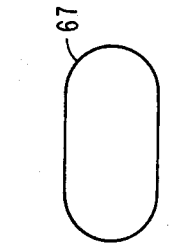
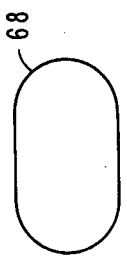
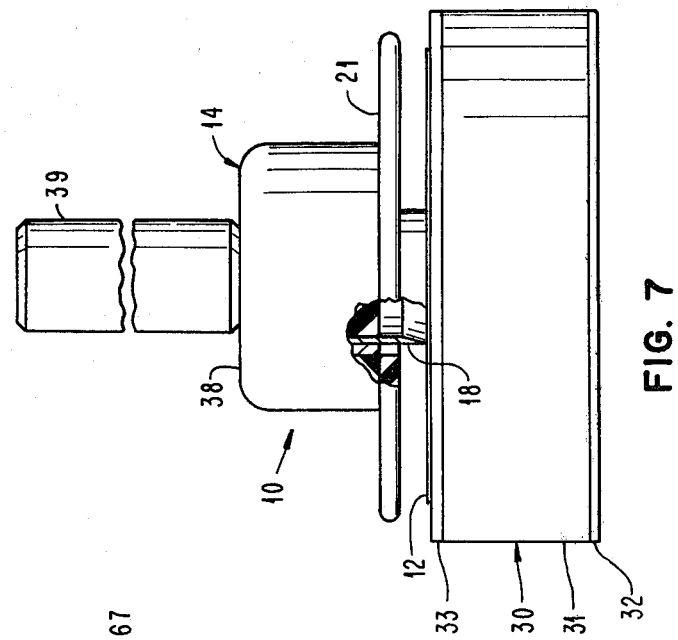

CUTTING APPARATUS FOR CUTTING A NON-CIRCULAR OPENING

This invention relates to a cutting apparatus for cutting a non-circular opening of a selected shape and, more particularly, to a cutting apparatus for cutting a non-circular opening of a selected shape in each of a face plate for a stoma and an adhesive blank utilized with the face plate.

An ostomy is a surgical operation in which a new outside opening is formed in an abdominal wall to permit removal of waste products from the body. This opening is called a stoma.

To collect the body wastes from the stoma, a person with the ostomy must wear an ostomy appliance, which is a collecting device. The collecting device includes a face plate and a bag supported on the face plate. The face plate must be positioned on the body relative to the stoma to prevent leakage from the stoma without exerting pressure on the stoma. The face plate is normally secured to the body by using an adhesive sealing element, which is initially part of an adhesive blank, to attach the face plate to the body in a sealing relationship with the stoma.

It is necessary for the opening in the face plate and the opening in the adhesive sealing element to be substantially the same shape and size as the stoma. Thus, each of the periphery of the opening in the face plate and the periphery of the opening in the sealing adhesive element are preferably about 1/32" larger than the periphery of the stoma.

Face plates are sold with various size circular openings therein to be used with various size stomas. Likewise, the adhesive blanks are available with circular openings of various diameters. If the adhesive blanks do not have an opening therein, U.S. Pat. No. 4,010,543 to Nusbaum discloses an apparatus for cutting a circular opening in the adhesive blank.

However, all stomas are not circular. They may be various non-circular shapes, particularly oval shapes.

When a person has a stoma of a non-circular shape, it is necessary for the person to form an opening in the face plate having the shape of the person's stoma. This requires the person to draw the outline of the opening on the face plate surface and then to cut the face plate along the outline with a pair of scissors, for example.

This also has required the user to place an adhesive blank, which includes the adhesive sealing element provided between the face plate and the body of the user to seal between the stoma and the face plate and attach the face plate to the body of the user, over the face plate and have the configuration of the opening in the face plate drawn on the adhesive blank by a pencil or pen, for example. Then, a pair of scissors is employed to cut the non-circular opening in the adhesive blank. The adhesive sealing element, which is part of the adhesive blank, must normally be replaced once or twice a week.

This is a time consuming task. It also requires the user to trace the outline of the non-circular opening, which has been formed in the face plate, correctly in order that the opening in the adhesive blank will be the correct size and shape.

The cutting apparatus of the present invention overcomes the foregoing problems through using a non-circular cutting element with the cutting element being capable of having the shape of most non-circular stomas. Thus, the cutting apparatus of the present invention would be manufactured with any of a plurality of cutting elements of different non-circular shapes so as to be capable of forming openings in the face plate and the adhesive blanks of the size and shape necessary for use with most, if not all, non-circular stomas.

The cutting apparatus of the present invention requires only a relatively short period of time to form the opening in the face plate and in each of the adhesive blanks. This is accomplished through disposing the cutting edge of the cutting element at the desired location on the face plate and then striking a body, which supports the cutting element, with a striking instrument one or more times.

When the adhesive blanks are to have the openings cut therein, a template is attached to the body, which supports the cutting element, to center the cutting element with respect to the adhesive blank. Again, the striking instrument is utilized to strike the body one or more times to cause the cutting element to cut the adhesive blank to form the non-circular opening of the desired shape therein.

An object of this invention is to provide a cutting apparatus for cutting selected non-circular shaped openings in a face plate and an adhesive blank for a stoma.

Another object of this invention is to provide a cutting apparatus having a cutting element with a precise non-circular shape.

Other objects of this invention will be readily perceived from the following description, claims, and drawings.

This invention relates to a cutting apparatus for cutting a non-circular opening in a face plate for a stoma including a body having a recess in one surface thereof. A non-circular cutting element is disposed within the recess and extends a selected distance beyond the one surface of the body. The non-circular cutting element, which has a selected non-circular shape, has its outer surface straight and its inner surface beveled to form the cutting surface of the non-circular cutting element. The non-circular cutting element is permanently retained in its desired position within the recess by retaining means.

The attached drawings illustrate a preferred embodiment of the invention, in which:

FIG. 7 is a schematic elevational view, partly in section, showing an opening about to be cut in the adhesive blank by the cutting apparatus of the present invention;

FIG. 8 is a schematic view of a circle from which various non-circular cutting shapes of the cutting element may be obtained;

FIGS. 8A, 8B, and 8C are schematic views of non-circular cutting shapes capable of being produced from the circle of FIG. 8;

FIG. 9 is a schematic view of another circle from which various non-circular cutting shapes of the cutting element may be obtained;

FIGS. 9A, 9B, 9C, and 9D are schematic views of non-circular cutting shapes capable of being produced from the circle of FIG. 9;

FIG. 10 is a schematic view of a further circle from which various non-circular cutting shapes of the cutting element may be obtained;

FIGS. 10A, 10B, 10C, 10D, 10E, and 10F are schematic views of non-circular cutting shapes capable of being produced from the circle of FIG. 10;

FIG. 11 is a schematic view of still another circle from which various non-circular cutting shapes of the cutting element may be obtained;

FIGS. 11A, 11B, and 11C are schematic views of non-circular cutting shapes capable of being produced from the circle of FIG. 11;

FIG. 12 is a schematic view of a still further circle from which various non-circular cutting shapes of the cutting element may be obtained; and FIGS. 12A, 12B, 12C, and 12D are schematic views of non-circular cutting shapes capable of being produced from the circle of FIG. 12.

Figure 1:
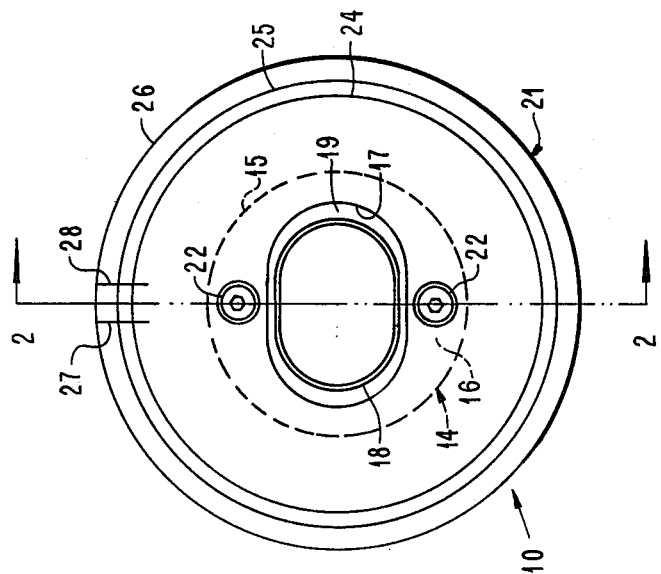
FIG. 1 is a front elevational view of a cutting apparatus of the present invention.
Figure 2:
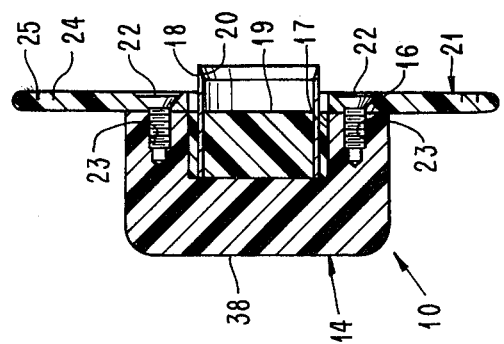
FIG. 2 is a sectional view of the cutting apparatus of FIG. 1 and taken along line 2—2 of FIG. 1.
Figure 3:
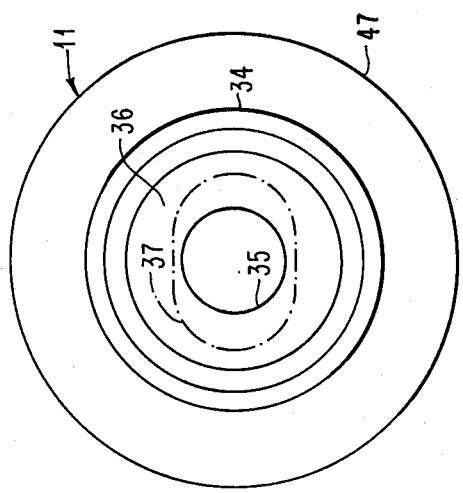
FIG. 3 is a plan view of a face plate to be cut by the cutting apparatus of the present invention.
Figure 4:
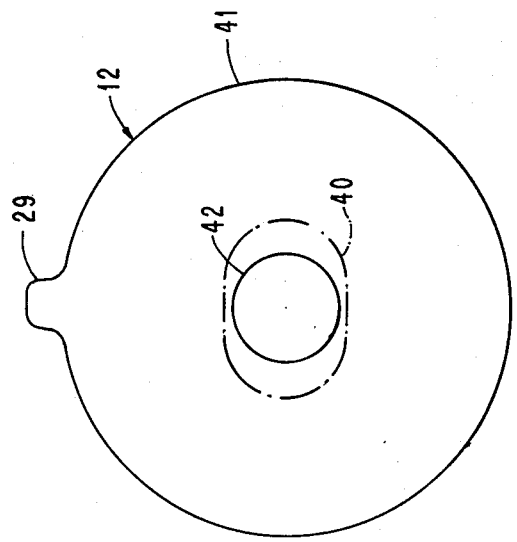
FIG. 4 is a plan view of an adhesive blank to be cut by the cutting apparatus of the present invention.

Referring to the drawings and particularly FIGS. 1 and 2, there is shown a cutting apparatus 10 of the present invention for cutting non-circular openings of the same size and shape in a face plate 11 (see FIG. 3), which is formed of any suitable material such as Hypalon, for example, and an adhesive blank 12 (see FIG. 4). The cutting apparatus 10 (see FIGS. 1 and 2) includes a body 14, which is formed of any suitable material such as nylon, for example.

The body 14 is circular and has a selected diameter to form a circumferential edge 15. In its flat surface 16, the body 14 has a recess 17 formed therein. A non-circular cutting element 18 is retained within the recess 17 by an epoxy 19. The recess 17 can be any shape but is preferably a non-circular shape and of slightly larger size than the cutting element.

The cutting element 18 is preferably formed of a tube of a selected length so that the cutting element 18 is capable of cutting both the face plate 11 (see FIG. 3) and the adhesive blank 12 (see FIG. 4). The cutting element 18 (see FIG. 2) has its inner surface 20 beveled to form the cutting edge of the cutting element 10. The beveled surface 20 is preferably at an angle of 15°.

The cutting element 18 has its outer surface straight. This outer surface provides an edge at the end of the beveled surface 20 to control the size and shape of the opening formed by the cutting element 18 in the face plate 11 (see FIG. 3) and the adhesive blank 12 (see FIG. 4).

The cutting element 18 (see FIGS. 1 and 2) is formed of any suitable material capable of cutting the face plate 11 (see FIG. 3) and the adhesive blank 12 (see FIG. 4). The cutting element 18 (see FIGS. 1 and 2) is preferably made of carbon steel, which is heat treated for hardening. Another example of the material of the cutting element 18 is stainless steel.

A circular template 21 is removably secured to the body 14. The template 21 is formed of any suitable transparent material such as a clear plastic, for example. One suitable example of the clear plastic is Plexiglas.

The template 21 is releasably retained on the body 14 and against the flat surface 16 of the body 14 by a pair of diametrically disposed screws 22 extending into a pair of diametrically disposed threaded openings 23 (see FIG. 2) in the body 14. Any other suitable means for releasably securing the template 21 to the body 14 may be employed. For example, the template 21 could have a pair of diametrically disposed arcuate slots with an enlarged opening at each end to enable fitting over a pair of diametrically disposed stud heads in the body 14. Then, a slight turning of the template 21 would result in the heads of the studs in the body 14 being disposed in the arcuate slots in the template 21 to retain the template 21 on the body 14.

The template 21 has a pair of circular lines 24 (see FIG. 1) and 25 formed therein. Each of the circular lines 24 and 25 has a diameter corresponding to one of the diameters of the adhesive blanks 12 (see FIG. 4), which are sold by United Division of Howmedica, Inc. as "Seal-Tite" gaskets. The template 21 (see FIG. 1) has its circumferential edge 26 of a diameter to correspond with the diameter of another of the "Seal-Tite" gaskets.

The template 21 has a pair of substantially parallel lines 27 and 28 therein and extending from the circumferential edge 26 to slightly beyond the inner circular line 24. The lines 27 and 28 are spaced from each other substantially the same distance as a tab 29 (see FIG. 4) on the adhesive blank 12. Thus, the lines 27 (see FIG. 1) and 28 enable alignment of the cutting apparatus 10 (see FIGS. 1 and 2) with the center of the adhesive blank 12 (see FIG. 4).

Figure 6:
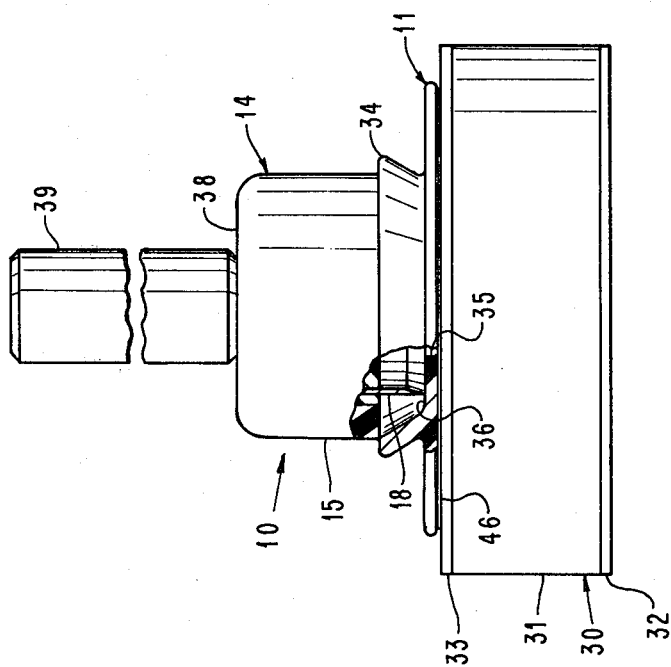
FIG. 6 is a schematic elevational view, partly in section, showing an opening about to be cut in the face plate by the cutting apparatus of the present invention.

When the cutting apparatus 10 (see FIG. 1) is to have the cutting element 18 cut a non-circular shaped opening in the face plate 11 (see FIG. 3), the face plate 11 is disposed on a support block 30 (see FIG. 6). The support block 30 may be formed of any suitable material or materials. One suitable example of the support block 30 is a block 31 of wood having a felt pad 32 on its bottom and a vinyl cover 33 on its top.

The cutting apparatus 10 is disposed so that the cutting element 18 extends within an annular flange 34 on the face plate 11. It should be understood that the face plate 11 has a circular opening 35 formed in its base 36. However, it is not a requisite for the face plate 11 to have the circular opening 35 therein in order for the cutting apparatus 10 to cut a non-circular shaped opening 37 (see FIG. 3) of the same configuration as the cutting element 18 (see FIG. 1) of the cutting apparatus 10.

The diameter of the body 14 of the cutting apparatus 10 is selected so that the circumferential edge 15 of the body 14 cooperates with the annular flange 34 (see FIG. 6) to allow the body 14 to be centered relative to the center of the face plate 11. The annular flange 34 supports the bag of the ostomy appliance with the bag being retained on the annular flange 34 by any suitable retaining means such as a drawstring, for example.

With the cutting apparatus 10 positioned as shown in FIG. 6, a substantially flat surface 38 of the body 14 is struck one or more times with a striking instrument 39, which may be a metal rod, for example, to cause the cutting element 18 to penetrate through the base 36 of the face plate 11. This forms the non-circular shaped opening 37 (see FIG. 3) in the face plate 11 with the opening 37 being about 1/32" larger than the stoma. Because of the flexibility of the annular flange 34 of the face plate 11, the circumferential edge 15 (see FIG. 1) of the body 14 moves inside of the annular flange 34 (see FIG. 6) of the face plate 11 when the cutting element 18 penetrates the base 36 of the face plate 11.

When it is desired to form a non-circular shaped opening 40 (phantom lines in FIG. 4) in the adhesive blank 12 of the same size and shape as the opening 37 (see FIG. 3) in the face plate 11, the template 21 (see FIGS. 1 and 2) is secured to the body 14 by the screws 22. Then, the adhesive blank 12 (see FIG. 7) is placed on top of the vinyl cover 33 of the support block 30. The template 21 has one of the circular lines 24 (see FIG. 1) and 25 or the circumferential edge 26 of the template 21 aligned with a circumferential edge 41 (see FIG. 4) of the adhesive blank 12. At the same time, the substantially parallel lines 27 (see FIG. 1) and 28 of the template 21 are aligned with the tab 29 (see FIG. 4) of the adhesive blank 12. Then, the flat surface 38 (see FIG. 7) of the body 14 of the cutting apparatus 10 is struck one or more times by the striking instrument 39. This produces the desired shaped opening 40 (see FIG. 4) in the adhesive blank 12.

It should be understood that the adhesive blank 12 (see FIG. 4) has a circular cut 42 formed at its center to enable removal of a central circular portion of the adhesive blank 12 to provide a circular opening. This is when the adhesive blank 12 is the "Seal Tite" gasket. It should be understood that it is not necessary for the adhesive blank 12 to have the circular cut 42 therein to enable formation of the non-circular shaped opening 40 therein.

Figure 5:
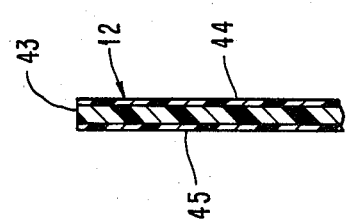
FIG. 5 is an enlarged fragmentary sectional view of the adhesive blank of FIG. 4.

As shown in FIG. 5, the adhesive blank 12 includes a central portion 43 and outer portions 44 and 45 on each side of the central portion 43. The central portion 43 has adhesive on each of its surfaces while each of the outer portions 44 and 45 has an adhesive inner surface abutting one of the adhesive surfaces of the central portion 43.

Therefore, to mount the adhesive blank 12 on the face plate 11 (see FIG. 6) on a surface 46 of the base 36 next to the body of the user, one of the two outer portions 44 (see FIG. 5) and 45 of the adhesive blank 12 is removed through grasping the tab 29 (see FIG. 4) of the outer portion 44 (see FIG. 5) or 45 to be removed. This exposes one of the adhesive surfaces of the central portion 43 to enable it to adhere to the surface 46 (see FIG. 6) of the base 36 of the face plate 11.

Then, the tab 29 (see FIG. 4) on the central portion 43 (see FIG. 5) of the adhesive blank 12 is bent over circumferential edge 47 (see FIG. 3) of the face plate 11. With the adhesive blank 12 (see FIG. 4) now secured to the face plate 11 (see FIG. 3), the tab 29 (see FIG. 4) of the other of the outer portions 44 (see FIG. 5) and 45 of the adhesive blank 12 is grasped to remove the other of the outer portions 44 and 45 from the central portion 43. This presents the other adhesive surface of the central portion 43 for adhering to the body of the user when the non-circular shaped opening 37 (see FIG. 3) in the face plate 11 is properly positioned relative to the stoma. Thus, the central portion 43 (see FIG. 5) of the adhesive blank 12 is an adhesive sealing element or ring between the face plate 11 (see FIG. 3) and the body of the user. Then, the bag of the ostomy appliance is attached to the annular flange 34 of the face plate 11.

The outer surface of the cutting element 18 (see FIG. 1) of the cutting apparatus 10 may have any of non-circular shapes 50 (see FIG. 8A), 51 (see FIG. 8B), and 52 (see FIG. 8C) formed from a circular shape 53 (see FIG. 8) having a diameter of 13/16". This results in the shape 50 (see FIG. 8A) having dimensions of ⅝" and 59/64", the shape 51 (see FIG. 8B) having dimensions of 11/16" and ⅞", and the shape 52 (see FIG. 8C) having dimensions of 9/16" and 61/64".

The outer surface of the cutting element 18 (see FIG. 1) may have any of non-circular shapes 54 (see FIG. 9A), 55 (see FIG. 9B), 56 (see FIG. 9C), and 57 (see FIG. 9D) formed from a circular shape 58 (see FIG. 9) having a diameter of ⅞". This results in the shape 54 (see FIG. 9A) having dimensions of ⅝" and 1 1/64", the shape 55 (see FIG. 9B) having dimensions of 11/16" and 63/64", the shape 56 (see FIG. 9C) having dimensions of ¾" and 61/64", and the shape 57 (see FIG. 9D) having dimensions of 13/16" and 29/32".

The outer surface of the cutting element 18 (see FIG. 1) may have any of non-circular shapes 59 (see FIG. 10A), 60 (see FIG. 10B), 61 (see FIG. 10C), 62 (see FIG. 10D), 63 (see FIG. 10E), and 64 (see FIG. 10F) formed from a circular shape 65 (see FIG. 10) having a diameter of 1". This results in the shape 59 (see FIG. 10A) having dimensions of 11/16" and 1 3/16", the shape 60 (see FIG. 10B) having dimensions of ¾" and 1 9/64", the shape 61 (see FIG. 10C) having dimensions of 13/16" and 1 7/64", the shape 62 (see FIG. 10D) having dimensions of ⅞" and 1 3/32", the shape 63 (see FIG. 10E) having dimensions of 9/16" and 1¼", and the shape 64 (see FIG. 10F) having dimensions of ⅝" and 1 7/32".

The outer surface of the cutting element 18 (see FIG. 1) may have any of non-circular shapes 66 (see FIG. 11A), 67 (see FIG. 11B), and 68 (see FIG. 11C) formed from a circular shape 69 (see FIG. 11) having a diameter of 1 1/16". This results in the shape 66 (see FIG. 11A) having dimensions of 9/16" and 1 11/32", the shape 67 (see FIG. 11B) having dimensions of ⅝" and 1 5/16", and the shape 68 (see FIG. 11C) having dimensions of 11/16" and 1 9/32".

The outer surface of the cutting element 18 (see FIG. 1) may have any of non-circular shapes 70 (see FIG. 12A), 71 (see FIG. 12B), 72 (see FIG. 12C), and 73 (see FIG. 12D) formed from a circular shape 74 (see FIG. 12) having a diameter of 1⅛". This results in the shape 70 (see FIG. 12A) having dimensions of 11/16" and 1⅜", the shape 71 (see FIG. 12B) having dimensions of ¾" and 1 11/32", the shape 72 (see FIG. 12C) having dimensions of 13/16" and 1 5/16", and the shape 73 (see FIG. 12D) having dimensions of ⅞" and 1 17/64".

It should be understood that the outer surface of the cutting element 18 (see FIG. 1) may have a plurality of non-circular shapes. Thus, the non-circular cutting element 18 is not limited to the configurations disclosed but may be any non-circular shape to which it may be formed.

An advantage of this invention is that it reduces the time to form a non-circular opening in each of a face plate and an adhesive blank, which includes an adhesive sealing element to be adhered to the face plate. Another advantage of this invention is that it enables a precise shaped opening, which conforms to a non-circular stoma, to be obtained in each of a face plate and an adhesive blank having an adhesive sealing element for utilization with the face plate.

For purposes of exemplification, a particular embodiment of the invention has been shown and described according to the best present understanding thereof. However, it will be apparent that changes and modifications in the arrangement and construction of the parts thereof may be resorted to without departing from the spirit and scope of the invention.

I claim:
1. A cutting apparatus for cutting a non-circular opening in a face plate for a non-circular stoma in which the face plate has an annular flange to support a bag of an ostomy appliance including:
- a body having a single recess in one surface thereof, said recess having a single continuous peripheral wall;
- a non-circular cutting element disposed within said recess and extending a selected distance beyond said one surface of said body;
- said body having a circular periphery to center said body relative to an annular flange of a face plate in which a non-circular opening is to be cut by said non-circular cutting element;
- said recess in said body having a non-circular shape substantially the same shape as said non-circular cutting element;
- said non-circular cutting element having a selected non-circular shape in accordance with the shape of the non-circular stoma with which the face plate is to be used;
- said non-circular cutting element having its outer surface straight and its inner surface beveled at its outer end to form the cutting surface of said non-circular cutting element;
- and retaining means to permanently retain said non-circular cutting element in its desired position within said recess.

2. The cutting apparatus according to claim 1 including:
- template means to center said non-circular cutting element relative to a face plate adhesive blank in which a non-circular opening is to be cut by said non-circular cutting element;
- said template means having an opening in its center through which said non-circular cutting element extends;
- said non-circular cutting element extending a selected distance beyond said template means at all times;
- and means to releasably secure said template means to said body against said one surface to enable removal of said template means when said non-circular cutting element is to cut a non-circular opening in a face plate.

3. The cutting apparatus according to claim 2 in which said template means includes a circular element of a transparent material having a plurality of circular lines thereon of selected diameters to center said non-circular cutting element relative to a face plate adhesive blank in which a non-circular opening is to be cut by said non-circular cutting element, each of said circular lines and the edge of said circular element has a diameter corresponding to the diameter of a face plate adhesive blank in which a non-circular opening is to be cut therein by said non-circular cutting element.

4. The cutting apparatus according to claim 3 including alignment means on said circular element to align said circular element with a tab on a face plate adhesive blank in which said non-circular cutting element is to be cut a non-circular opening at the center thereof.

5. The cutting apparatus according to claim 4 in which said alignment means includes a pair of substantially parallel lines extending from the edge of said circular element to at least the inner of said circular lines.

6. The cutting apparatus according to claim 5 in which said retaining means is an epoxy.

7. The cutting apparatus according to claim 4 in which said retaining means is an epoxy.

8. The cutting apparatus according to claim 3 in which said retaining means is an epoxy.

9. The cutting apparatus according to claim 2 in which said retaining means is an epoxy.

10. The cutting apparatus according to claim 1 in which said retaining means is an epoxy.

11. The cutting apparatus according to claim 6 in which:
- said recess has its bottom wall engaged by said non-circular cutting element;
- and said non-circular cutting element has its outer surface spaced from the peripheral wall of said recess.

12. The cutting apparatus according to claim 6 in which said non-circular cutting element is a single hollow tube.

13. The cutting apparatus according to claim 6 in which said cutting surface of said non-circular cutting element has a length less than the selected distance that said non-circular cutting element extends beyond said template means.

14. The cutting apparatus according to claim 2 in which said cutting surface of said non-circular cutting element has a length less than the selected distance that said non-circular cutting element extends beyond said template means.

15. The cutting apparatus according to claim 2 in which said opening in said template means is the same size and shape as the peripheral wall of said recess in said body.

16. The cutting apparatus according to claim 1 in which:
- said recess has its bottom wall engaged by said non-circular cutting element;
- and said non-circular cutting element has its outer surface spaced from the peripheral wall of said recess.

17. The cutting apparatus according to claim 1 in which said non-circular cutting element is a single hollow tube.

18. The cutting apparatus according to claim 1 in which the selected non-circular shape of said non-circular cutting element is an oval shape.

19. A cutting apparatus for cutting a non-circular opening in a face plate for a non-circular stoma in which the face plate has an annular flange to support a bag of an ostomy appliance including:
- a body having a single recess in one surface thereof, said recess having a single continuous peripheral wall;
- a non-circular cutting element disposed within said recess and extending a selected distance beyond said one surface of said body;
- said non-circular cutting element being a single hollow tube;
- said recess having its bottom wall engaged by said non-circular cutting element;
- said non-circular cutting element having its outer surface spaced from the peripheral wall of said recess;
- said body having a circular periphery to center said body relative to an annular flange of a face plate in which a non-circular opening is to be cut by said non-circular cutting element;
- said recess in said body having a non-circular shape substantially the same shape as said non-circular cutting element;
- said non-circular cutting element having a selected non-circular shape in accordance with the shape of the non-circular stoma with which the face plate is to be used;

said non-circular cutting element having its outer surface straight and its inner surface beveled at its outer end to form the cutting surface of said non-circular cutting element;

an epoxy to permanently retain said non-circular cutting element in its desired position within said recess, said epoxy filling said recess on both sides of said non-circular cutting element;

template means to center said non-circular cutting element relative to a face plate adhesive blank in which a non-circular opening is to be cut by said non-circular cutting element;

said template means having an opening in its center through which said non-circular cutting element extends;

said non-circular cutting element extending a selected distance beyond said template means at all times;

means to releasably secure said template means to said body against said one surface to enable removal of said template means when said non-circular cutting element is to cut a non-circular opening in a face plate;

said template means including a circular element of a transparent material having a plurality of circular lines thereon of selected diameters to center said non-circular cutting element relative to a face plate adhesive blank in which a non-circular opening is to be cut by said non-circular cutting element, each of said circular lines having a diameter corresponding to the diameter of a face plate adhesive blank in which a non-circular opening is to be cut therein by said non-circular cutting element;

alignment means on said circular element to align said circular element with a tab on a face plate adhesive blank in which said non-circular cutting element is to cut a non-circular opening at the center thereof;

and said alignment means includes a pair of substantially parallel lines extending from the edge of said circular element to at least the inner of said circular lines.

* * * * *

UNITED STATES PATENT AND TRADEMARK OFFICE
CERTIFICATE OF CORRECTION

PATENT NO. : 4,391,042
DATED : July 5, 1983
INVENTOR(S) : Ned E. Sunderland

It is certified that error appears in the above—identified patent and that said Letters Patent is hereby corrected as shown below:

Column 7, line 57, cancel "be."

Signed and Sealed this

Thirtieth Day of August 1983

[SEAL]

Attest:

Attesting Officer

GERALD J. MOSSINGHOFF

Commissioner of Patents and Trademarks